United States Patent

Hood et al.

Patent Number: 6,143,011
Date of Patent: Nov. 7, 2000

[54] HYDROKERATOME FOR REFRACTIVE SURGERY

[75] Inventors: Larry L. Hood, Laguna Hills; Rex E. Doherty, Orinda; William T. Hood, Anaheim, all of Calif.

[73] Assignee: SurgiJet, Inc., Irvine, Calif.

[21] Appl. No.: 09/058,791

[22] Filed: Apr. 13, 1998

[51] Int. Cl.$^7$ .................................................. A61F 9/00

[52] U.S. Cl. ............................................................ 606/166

[58] Field of Search ...................................... 606/166, 170

[56] References Cited

U.S. PATENT DOCUMENTS

| | | | |
|---|---|---|---|
| 4,024,866 | 5/1977 | Wallach | 128/276 |
| 4,936,850 | 6/1990 | Barrett | 623/6 |
| 5,556,406 | 9/1996 | Gordon et al. | 606/166 |
| 5,643,299 | 7/1997 | Bair | 606/166 |

*Primary Examiner*—Michael Buiz
*Assistant Examiner*—Vy Q. Bui
*Attorney, Agent, or Firm*—Harris Zimmerman

[57] ABSTRACT

An apparatus for guiding a high speed liquid jet used in forming ophthalmic incisions includes an instrument body having an elongated rectangular portion and a tapered end portion. A cylindrical housing is secured to the tapered end, and is provided with a stepped opening extending axially therethrough. A jet carrier includes a longitudinally extending body, and a pair of high precision crossed roller slides join the carrier and body to permit lateral translation of the jet carrier. A micro-motor assembly secured within the rectangular body portion is joined to a pinion gear which engages a rack gear joined to the jet carrier to drive the jet carrier in lateral translation. The jet carrier includes a proximal connector for a high pressure fluid hose, and a jet nozzle assembly extending from the distal end. A plurality of guide members are provided, all having common structural features adapted to engage the stepped opening of the distal end of the instrument body. Each guide member includes a generally cylindrical body and a central portion comprised of a reticle and applanation plate, with differing guide members having applanation plates of various thicknesses. The guide member may include an adaptive applanator member that is selectively variably curved. The cylindrical body also includes an annular vacuum suction ring to selectively secure the device on the eye. The guide member has a jet slot extending in the sidewall thereof to receive the jet nozzle.

42 Claims, 8 Drawing Sheets

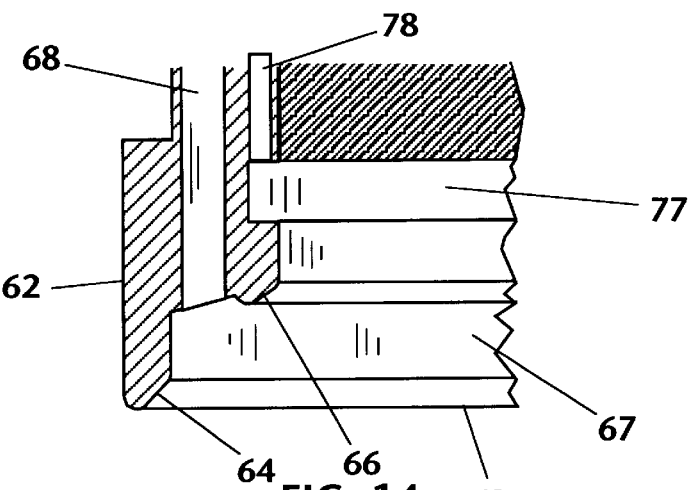
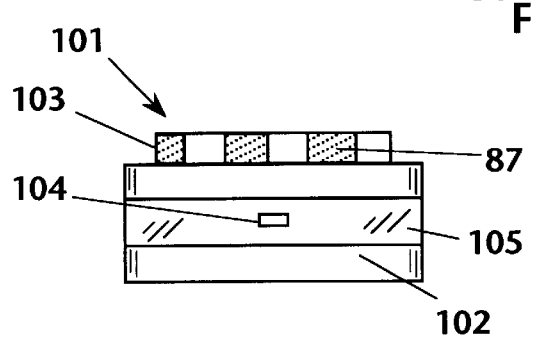
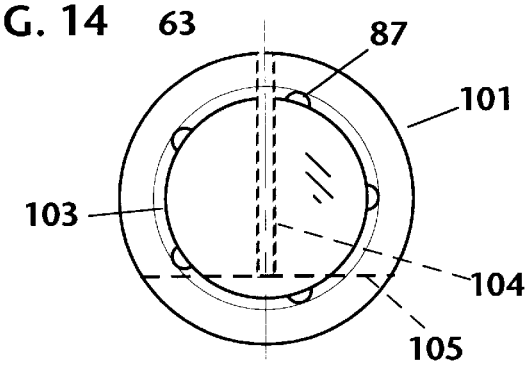
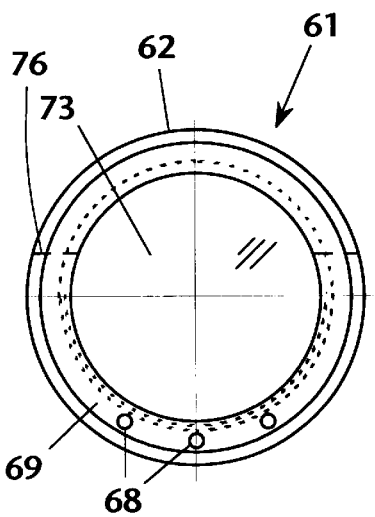
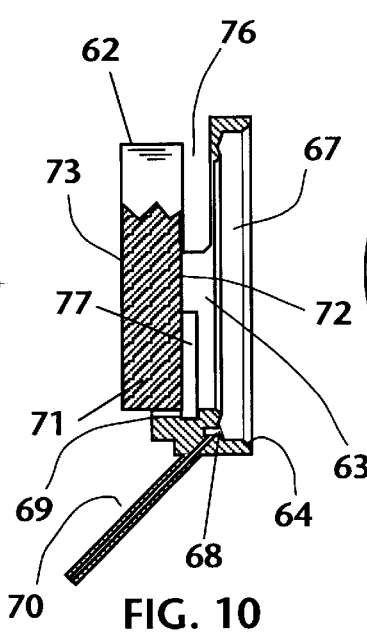
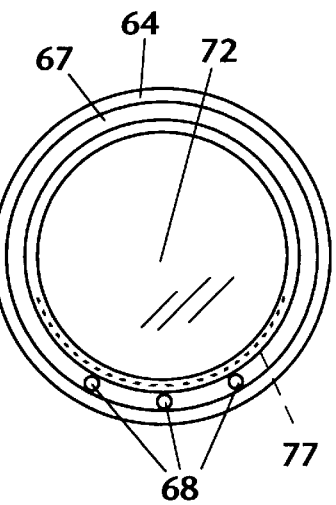

HYDROKERATOME FOR REFRACTIVE SURGERY

BACKGROUND OF THE INVENTION

The present invention relates to hydrogel surgical devices, and more particularly to hydrogel devices used for refractive surgery.

In recent years the use of surgical techniques for correction of ophthalmic refractive malfunction has progressed from experimental laboratory operations to widely accepted, commonplace procedures. Radial keratotomy (RK), photorefractive keratotomy (PRK), and myopic keratomileusis (MKM) have all become routine techniques in ophthalmology. Such aggressive surgical treatment is a relatively new development in ophthalmology. however, many patients require good uncorrected visual acuity for various occupations, such as pilots or professional athletes, and other patients seek good uncorrected visual acuity for cosmetic or psychological reasons. Moreover, some patients have subnormal vision, even when optimally corrected with spectacles or contact lenses, and seek surgical correction for improved vision.

Some photorefractive surgical techniques involve a lamellar keratotomy, in which a hinged flap of apical corneal tissue is created by incision in the cornea generally perpendicular to the primary visual axis. A second cut is then made, in which a thin wafer of stroma is removed. The flap is then returned to its initial position and permitted to heal in place. Removal of the thin wafer of stroma alters the conformation of the corneal apex, thereby modifying the refractive characteristics of the cornea. Clearly, the placement and formation of the second cut, as well as the thickness and planarity of the first incision, are crucial to the success of this technique.

Lamellar keratotomy has been performed using a microkeratome device, in which a high speed oscillating head supports a blade that creates the corneal cuts. However, the blade thickness, as well as the mechanical vibration and motion of the moving cutter limits the fineness and planarity of the incision, which in turn limits the potential for successful outcome of the surgery.

The use of surgical lasers has been approved by the U.S. FDA for carrying our lamellar keratotomy, in a procedure known by the acronym LASIK. A laser beam cuts tissue by forming a very narrow beam of light, and sweeping the beam through the corneal tissue. The energy density within the beam is sufficient to vaporize any cellular structure in its path, and the mechanism of the laser cutting process is essentially thermal pyrolysis. There is the opportunity for byproducts of tissue heating and burning to be formed in the process, and these byproducts can adversely affect the healing process of the surgical wound.

Recently, a high speed water jet has been used in lamellar keratotomy, in a technique termed hydrorefractive keratoplasty (HRK). A water jet having a diameter less than 50 $\mu$m is used to form the corneal incisions. The water jet is far smaller in diameter than the thickness of a cutting blade, whereby the incisions may be much finer, resulting in less tissue trauma, better healing, and greater potential for success. Also, the water jet cuts, delaminates, and separates tissue by imparting very high kinetic energy; unlike laser cutting, there is no formation of byproducts of tissue oxidation and burning.

The water jet is a linear "beam" which must be swept through the corneal tissue to effect the necessary incisions. The mechanism to effect the beam movement consists generally of a track on which the water jet nozzle is mounted in slidable fashion. The prior art demonstrates a need for an improved mechanism for guiding a water jet cutting beam with greater resolution and control, and for controlling the thickness of the cut and the thickness and conformation of the stromal wafer.

SUMMARY OF THE INVENTION

The present invention generally comprises an apparatus for supporting and guiding the movement of a high speed liquid jet used for cutting, particularly in the formation of ophthalmic incisions. A salient feature of the apparatus is that it eliminates the mechanical free play of prior art sliding or rolling devices, thereby taking full advantage of the extremely fine cutting beam produced by a high pressure cutting jet, and forming incisions of unprecedented planarity and thinness.

The apparatus includes an instrument body, comprised of an elongated rectangular portion and a tapered end portion extending distally therefrom. A cylindrical housing is secured to the tapered end, and is provided with a stepped opening extending axially therethrough. A bottom surface of the rectangular portion is provided with a pair of channels extending laterally in parallel, spaced apart configuration, and a pair of high precision crossed roller slides is secured in the pair of channels. Within the rectangular body portion, a micro-motor assembly is secured, including a shaft encoder, a gear box, and a pinion gear secured to the output of the gear box and extending generally between the crossed roller slides.

A liquid jet carrier includes a longitudinally extending body having a pair of channels extending laterally therein to receive the crossed roller slides in slidably translating fashion. A drive slot extends parallel to one of the crossed roller slides, and is disposed to receive the pinion gear of the micro-motor assembly. A rack gear also extends into the drive slot, and is engaged by the pinion gear to drive the jet carrier in lateral translation riding on the crossed roller slides. The jet carrier includes a proximal connector for a high pressure fluid hose, and a jet nozzle assembly extending from the distal end of the carrier. The encoder enables high precision movement and positioning of the jet carrier in the lateral direction.

The apparatus includes a plurality of guide members, all having common structural features adapted to engage the stepped opening of the distal end of the instrument body. Each guide member includes a generally cylindrical body, and the central portion comprises a reticle and applanation plate, both formed integrally of transparent plastic, so that the surgical site may be visualized directly therethrough. Differing guide members are provided with applanation plates of various thicknesses. The cylindrical body also includes an annular vacuum suction ring having a smoothly beveled annular opening disposed to impinge on an annular zone of the eye surrounding the cornea. The suction ring is connected to a vacuum source to selectively secure the device on the eye and establish a fixed position with respect thereto.

The guide member further includes a jet slot extending in the sidewall thereof perpendicular to the axis of the cylindrical housing. The slot subtends an angle less than 180°, and is disposed to receive the distal end of the jet nozzle assembly with minimum clearance for lateral translation in a chordal path. An aspiration groove is formed within the guide member in diametrical opposition to the slot to aspirate and remove the liquid and tissue debris generated by the liquid jet. The aspiration groove is also connected to a vacuum aspiration source.

To use the apparatus of the invention, a guide member having the desired applanation characteristics and thickness is selected and installed in the stepped opening of the instrument. The guide members and the stepped opening are provided with quick connect, self-aligning features that assure rapid installation at the proper angular orientation. The apparatus is properly position by visual inspection, using the reticle of the guide member, and the suction ring is connected to a vacuum source to secure the apparatus at the selected position on the eye. Thereafter, the jet nozzle is translated to a start position, and high pressure fluid is delivered to the jet nozzle to form a high pressure, high velocity jet beam of vary narrow diameter. The micro-motor assembly is actuated concurrently with the jet to translate the jet laterally through a portion of the corneal stroma and form a planar incision therein that defines a corneal apical flap. This process is then repeated to form a second incision at a second plane, defining a wafer of corneal stroma tissue that is then removed. The apical flap is then impinged on the incision surface and secured (or not) to permit healing and reattachment of the flap. The resection creates a new corneal curvature that alters the refractive characteristics of the eye.

The thickness of the applanation plate and its planarity or curvature determine the position and curvature of any incision made therewith, and proper selection of these parameters established the corrective factor for the procedure. The very high precision construction of the apparatus provides extreme accuracy in the placement and planarity of the incisions, and the narrow, high velocity water jet forms an incision with minimal loss of corneal tissue, free of any thermal effects.

Alternatively, the invention provides an adaptive applanator assembly that presents a selectively variably curved surface to impinge on the cornea. The adaptive applanator assembly may be set to assume a first curvature prior to a first incision, and subsequently reconfigured to assume a second curvature prior to a second incision, whereby the two incision may form a lenticular tissue wafer of predetermined thickness and curvature. This process may be carried out without moving the applanator assembly, thereby obviating difficulties in recentration, apical flap movement, and the like.

BRIEF DESCRIPTION OF THE DRAWINGS

FIG. 9 is a top view of the guide member of the invention.

FIG. 10 is a partially sectioned side elevation of the guide member shown in FIG. 9.

FIG. 11 is a bottom view of the guide member shown in FIGS. 9 and 10.

FIG. 12 is a top view of a calibration block for the jet nozzle, showing an optional quick connect feature.

FIG. 13 is a side elevation of the calibration block of FIG. 12.

FIG. 14 is an enlarged fragmentary cross-sectional view of the conformation of the suction ring and aspiration groove of the guide members.

DESCRIPTION OF THE PREFERRED EMBODIMENT

Figure 3:
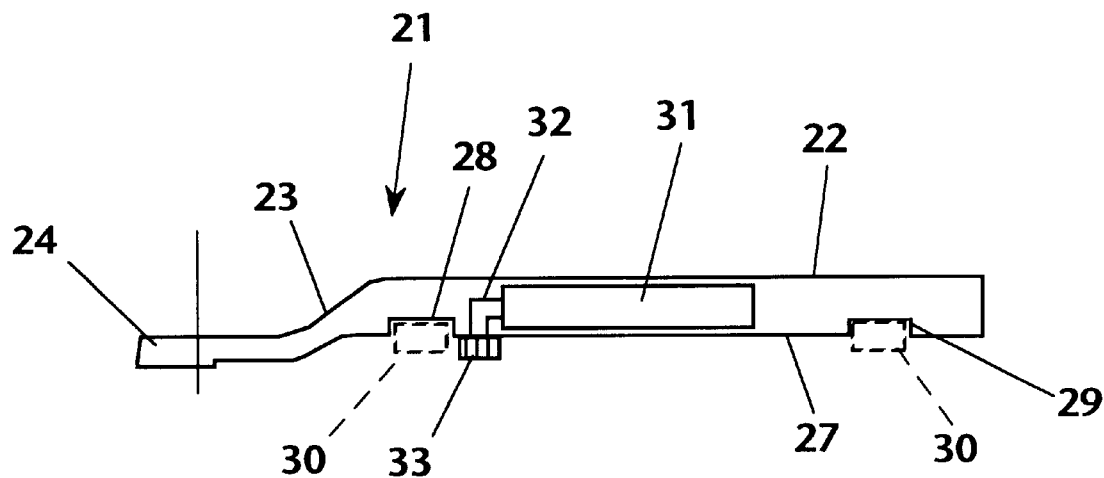
FIG. 3 is a side elevation of the instrument body of the ophthalmic surgical apparatus of the invention.
Figure 4:
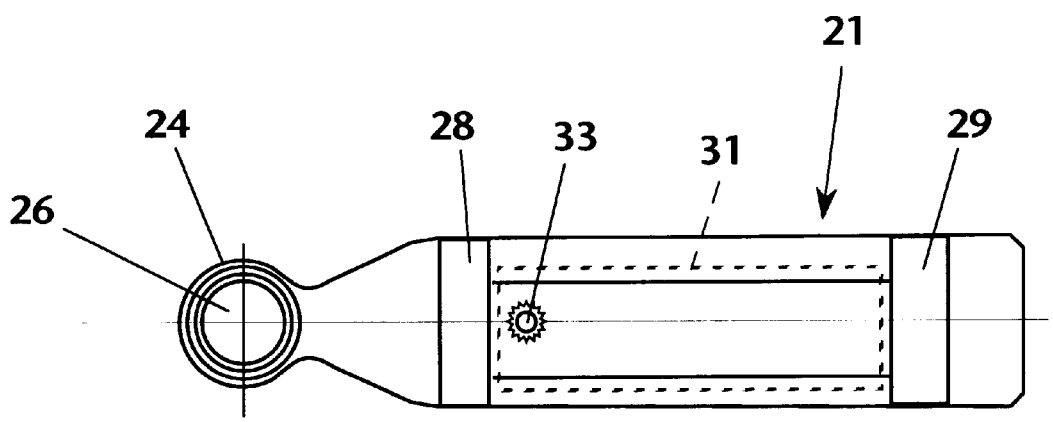
FIG. 4 is a bottom view of the instrument body of the opthalmic surgical apparatus of the invention.

The present invention generally comprises an apparatus for supporting and guiding the movement of a high speed liquid jet used for cutting, particularly in the formation of ophthalmic incisions. With regard to FIGS. 3–5, the apparatus includes an instrument body 21 having a longitudinally extending rectangular portion 22 and a tapered end portion 23 extending distally from the rectangular portion. A cylindrical housing 24 is joined to the tapered end portion 23, and is provided with a stepped opening 26 extending coaxially therethrough. A plurality of instrument bodies 21 may be provided, each having a different angular relationship (in the range of 5°–90°, 0°–20° preferred) between the portions 22 and 24 to accommodate differing eye inset physiognomy. Disposed in the bottom surface 27 of the portion 22 is a pair of channels 28 and 29 extending laterally in longitudinally spaced, parallel fashion. The channels 28 and 29 are generally orthogonal to the longitudinal axis of the body 21 and to the axis of the cylindrical housing 24. A pair of high precision crossed roller slides 30 are secured in the pair of channels 28 and 29.

Secured within the rectangular portion 22 of the instrument body is a micro-motor assembly 31 comprised of an electrical motor, a shaft encoder, and a gear reduction box. The output of the assembly 31 is coupled to a right angle drive 32, and a pinion gear 33 is secured to the output shaft of the right angle drive. The pinion gear projects from the bottom surface 27, and is disposed adjacent to the channel 28.

Figure 6:
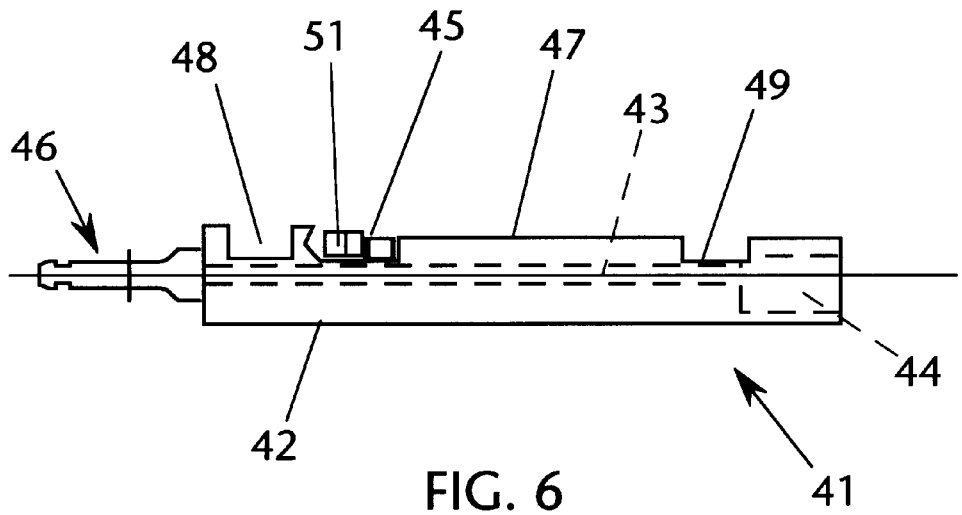
FIG. 6 is a side elevation of the jet carrier of the opthalmic surgical apparatus of the invention.
Figure 7:
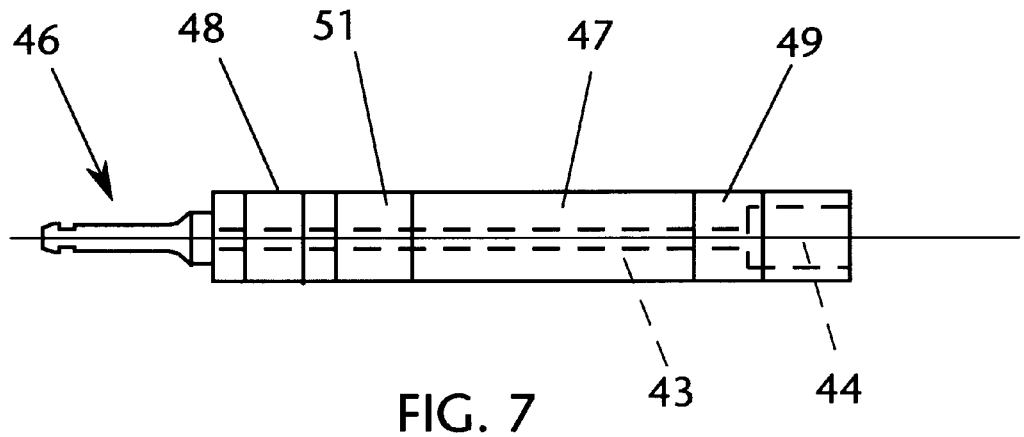
FIG. 7 is a top view of the jet carrier of the ophthalmnic surgical apparatus of the invention.
Figure 8:
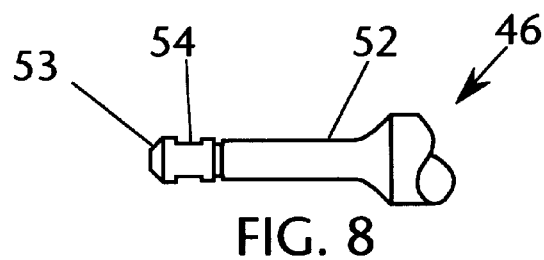
FIG. 8 is an enlarged detailed view of the jet nozzle assembly of the jet carrier of the ophthalmic surgical apparatus of the invention.

The apparatus further includes a jet carrier assembly 41, as shown in FIGS. 6–8. A jet carrier body 42 extends along a longitudinal axis, and includes a fluid passage 43 extending axially therethrough from a connector port 44 to a jet assembly 46 at the distal end thereof. The body 42 may also incorporate a fluid pressure amplifying mechanism, such as a piston intensifier, as is known in the prior art. Disposed in the top surface 47 of the body 42 is a pair of channels 48 and 49 extending laterally in longitudinally spaced, parallel fashion. The channels 48 and 49 are generally orthogonal to the longitudinal axis of the body 42 and are disposed parallel to the pair of channels 28 and 29 (FIG. 3 and 4) to secure the pair of high precision crossed roller slides 30, whereby the jet carrier may be translated laterally with respect to the instrument body 21 which is fixedly positioned relative to the eye undergoing a surgical procedure. A channel 51 extends adjacent and parallel to the channel 48, and is dimensioned to receive a rack gear 45 therein, together with a pinion gear 33, as will be detailed below.

To provide Z-axis control and precision variability of the hydrogel, one or more piezoelectric pads may be interposed between the crossed roller slides and the instrument body, and connected to a variable voltage source. The Z-axis range of motion required for resection of the cornea for refractive purposes is extremely small, and such piezo actuators (or the like) are well known in the prior art.

The jet assembly 46 includes a jet tube 52 extending distally and terminating in a removable end cap 53. The end cap 53 secures the jet orifice that emits a high velocity, ultra-fine stream of liquid, and is provided with wrench flats 54 to enable removal and replacement of the jet orifice and end cap. An aiming beam may be provided by a collimated LED or laser diode device secured to the end cap and aligned generally coaxially with the orifice.

Figure 8A:
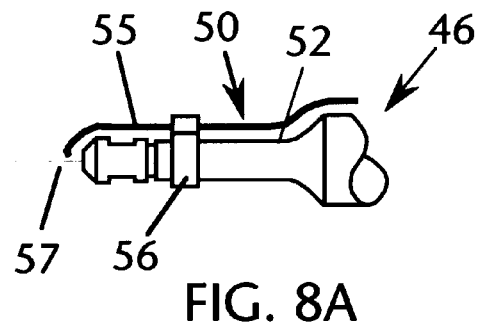
FIG. 8A is an enlarged detailed view of a further embodiment of the jet nozzle assembly of the jet carrier.

With regard to FIG. 8A, an alternative embodiment of the jet assembly 46 includes the structures described in FIG. 8, as well as a safety shutoff assembly 50. The assembly 50 includes a sheathed cable 55 secured to the jet tube 52 by bracket 56, the cable 55 being a bowden or brake cable construction that permits the selective advancement of an interior flexible cable with the outer sheath, as is known in the prior art. The distal end 57 of the cable assembly 55 is hooked, and disposed to intersect the liquid jet path closely adjacent to the output end of the jet assembly. The cable 55 is biased to extend and occlude the jet path; actuation of a manual or machine override mechanism is required to clear the jet path, thereby preventing unintentional firing of the jet.

The apparatus further includes a plurality of surgical guide members 61, as shown in FIGS. 9–11, the guide members all having common structural features adapted to engage the stepped opening 26 of the housing 24. Each guide member 61 includes a generally cylindrical body 62 having a stepped outer conformation. At the lower end, there is disposed a generally cylindrical opening 63 defined by a peripheral rim 64. As shown in FIG. 14, the rim 64 is beveled, and an inner lip 66 is disposed concentrically within the rim 64 and radially and axially inset therefrom to define an annular suction ring 67. A plurality of holes 68 extend from the suction ring 67 parallel to the axis of the cylindrical body 62 and opening at the outer annular surface 69 of the body 62. The holes 88, which extend in registration to fluid passages in housing 24 connected to port 91, supply vacuum pressure to the suction ring, so that it selectively adheres to a selected portion of the eyeball undergoing surgery. Alternatively, a short tube 70 may extend from the member 61 to secure a vacuum tube while also acting as a handle for the surgeon to steady the assembly.

At the opposite, upper end of the body 62 there is disposed a disk-like member 71 (see also FIG. 1) formed of transparent plastic material such as Lexan, methyl methacrylate, or similar material having high transparency and clarity and dimensional stability. The member 71 is provided with a lower surface 72 that is adapted to impinge on the central surface of the cornea to provide an applanation function. Accordingly the surface 72 may be provided with a predetermined curvature that falls within a range including plus and minus curves, planarity, and cylinder curves. Likewise, the thickness of the member 72 may be selectively varied to control the distance between the center line of the jet assembly 46 and the surface 72, so that the thickness of the corneal wafer cut may be carefully determined. The upper surface 73 is provided with a reticle 74 (FIG. 2) to facilitate centering the assembly on the cornea and controlling applanation and the surgical incisions. The plurality of members 71 are premanufactured with a wide range of curvature and thicknesses, whereby an appropriate guide member is available for the vast majority of refractive surgical procedures. Alternatively, the member 71 may be threaded into the body 62 and selectively rotated manually or by gear motor drive to selectively vary the thickness of the corneal wafer formed during surgery, as described below.

Figure 1:
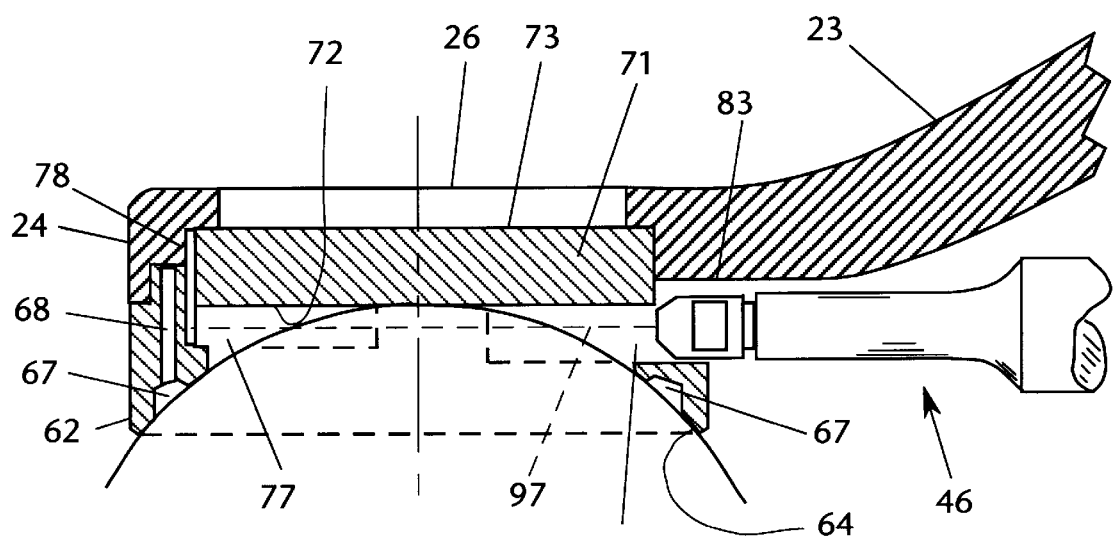
FIG. 1 is a magnified cross-sectional elevation showing the guide member mounted with the jet nozzle of the ophthalmic surgical apparatus of the invention for a surgical procedure on a typical eye.
Figure 2:
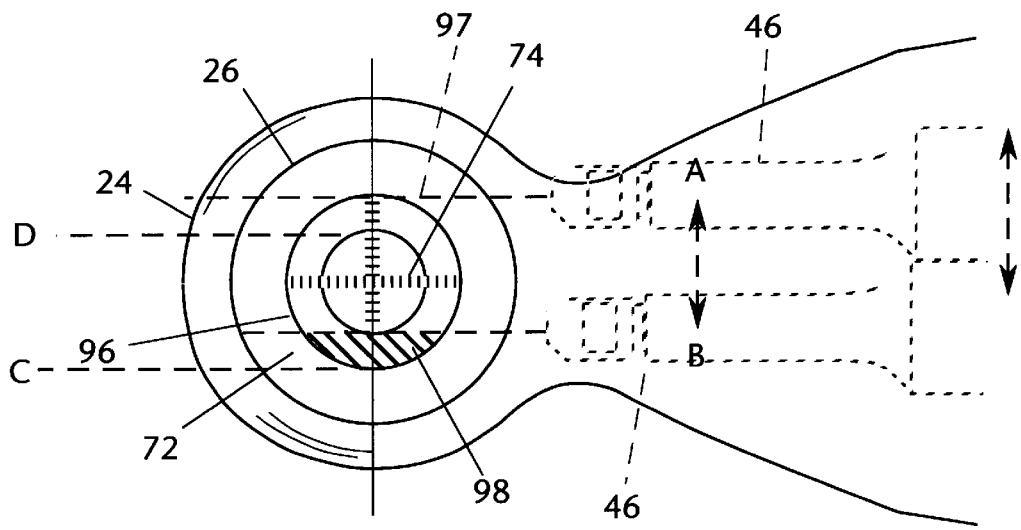
FIG. 2 is a magnified top view as in FIG. 1, showing movement of the jet nozzle with respect to the instrument body and patient eye.

The guide member body 62 further includes a jet slot 76 extending through a portion of the sidewall and perpendicular to the axis thereof, the jet slot extending chordally and subtending an angle less than 180°. As shown in FIG. 1, the slot 76 is sufficiently wide to receive the distal end 53 of the jet nozzle assembly 46 with minimal clearance for lateral translation in a chordal path. The guide member further includes an aspiration groove 77 formed annularly within the opening 63 and disposed in diametrical opposition to a medial portion of the slot 76. The aspiration groove 77 is connected to aspiration passages 78 so that liquid and tissue debris from the liquid jet is captured and removed from the surgical area. The vacuum supply and debris aspiration apparatus coupled to aspiration groove 77 is independent of the vacuum supply connected to the suction ring 67.

Figure 15:
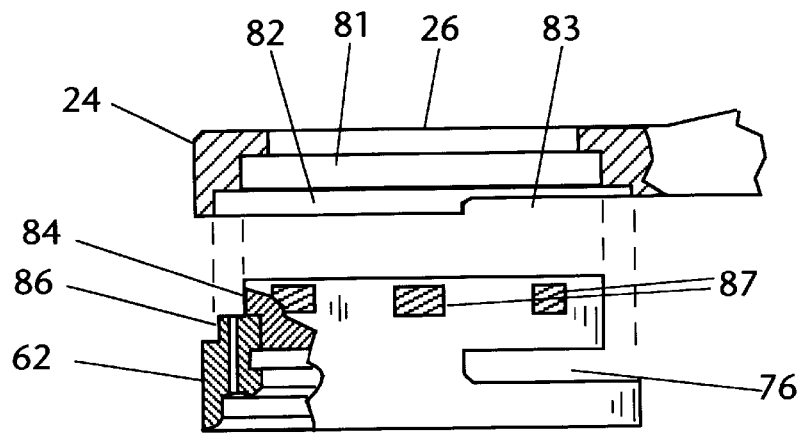
FIG. 15 is an exploded side elevation of the guide member and the distal end of the instrument body.

With regard to FIG. 15, the stepped opening 26 of the cylindrical housing 24 includes a medial internal annulus 81 and a lower internal annulus 82, both disposed coaxially with the upper opening 26. The upper cylindrical portion 84 of the guide member 61 is dimensioned for close tolerance fit in annulus 81, and the medial cylindrical portion 86 is dimensioned for close tolerance fit in annulus 82. A cutout 83 extends laterally in the lower surface of the housing 24, and is aligned in registration with the jet slot 76 of a guide member 61 when installed in the housing 24.

The cylindrical housing 24 and guide members 61 are also provided with a quick connect mechanism that enables installation and removal of each guide member rotation of the guide member through a small angle, and also align the guide member with the longitudinal axis of the instrument body with high precision. One such mechanism includes a plurality of lugs 87 extending from the portion 84 in angularly spaced array, each lug 87 including respective portions of annular threads. The internal annulus 81 is provided with a like plurality of recesses and threaded grooves (not shown) that receive the lugs and engage the threads thereof, whereby insertion of a guide member 61 into the lower opening 82 and a small angle rotation secures the guide member in the instrument body. Alignment indicia on the guide members and the housing 24 may be provided to facilitate proper installation. Other quick connect mechanisms known in the prior art may also be used.

Figure 5:
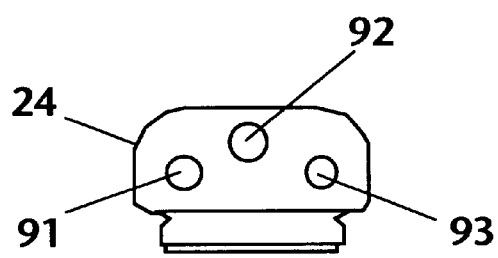
FIG. 5 is a distal end view of the instrument body of the ophthalmnic surgical apparatus of the invention.

With regard to FIG. 5, the cylindrical housing 24 includes a plurality of ports for connection to external service devices. Port 91 comprises a suction connector, and connected by internal passages to the vacuum passage 68 and the suction ring 67. Electrical connections to the instrument (power, servo control, illumination, etc.) are made through electrical jack 92. Port 93 comprises an aspiration connector that is connected to the aspiration groove 77.

Figure 16:
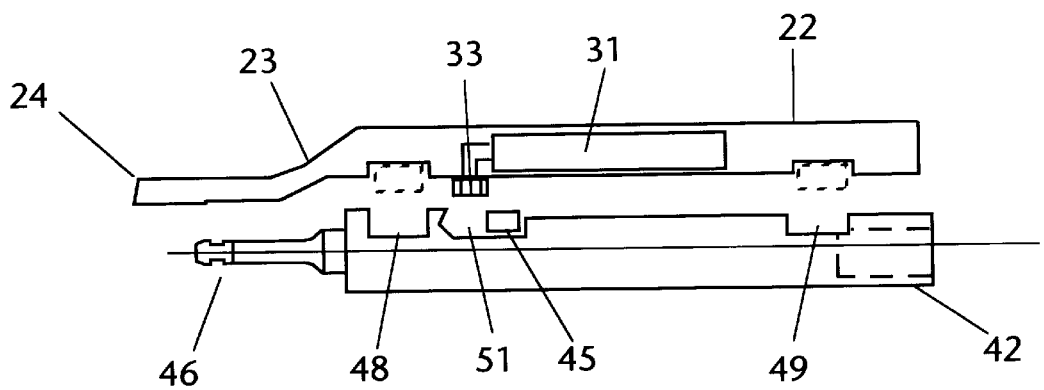
FIG. 16 is an exploded side elevation of the instrument body and the jet carrier of the invention.
Figure 17:
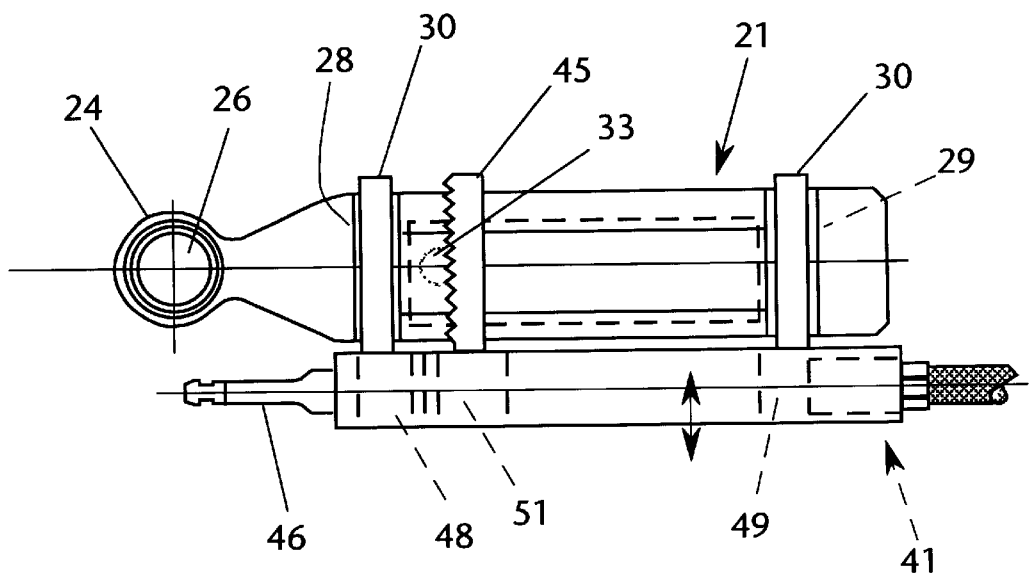
FIG. 17 is an exploded bottom view of the instrument body and the jet carrier of the invention.

With reference to FIGS. 16 and 17, the jet carrier 41 is disposed subjacently to the instrument body 21, with the channels 48 and 49 aligned with the channels 28 and 29 of the instrument body and the micro-precision crossed roller slides 30 disposed therebetween. The pinion gear 33 extends into the channel 51 to engage the rack gear 52 secured therein. The precision alignment of the crossed roller slides, together with a servo loop that controls operation of the micro-motor assembly 31 based on the shaft encoder signals, may control lateral movement and position of the jet carrier to an accuracy of approximately one micron.

To use the apparatus of the invention, a guide member 61 having the desired applanation characteristics and thickness is selected and installed in the opening 26, using the quick connect mechanism. With regard to FIGS. 1 and 2, the instrument body is then placed directly over the cornea of the eye, and aligned therewith by visualization of the reticle 74 with respect to the corneal margins. The applanated portion 94 of the corneal surface is measured for sufficiency, and vacuum pressure is then applied to the port 91. The rim 64 and lip 66 of suction groove 67 are disposed to impinge on an annular zone of the eye, fixing the instrument in the carefully aligned position. The interior opening 63 of the guide member 61 remains at standard pressure, as the vacuum is confined within the groove 67.

The micro-motor assembly 31 is then actuated to translate the jet carrier 41 laterally to the start position A. Aspirant suction is applied to port 93, high pressure liquid is supplied through connector 44 to jet assembly 46, and the high velocity jet beam 97 is formed. At the same time, the micro-motor assembly is actuated to move the jet carrier laterally to position B, causing the high velocity jet 97 to move through the corneal tissue and form a highly planar, precisely placed incision. Alternatively, the jet carrier can be translated from C to D, or from C to A, in accordance with the surgeon's plan. A portion 98 of the tissue in the incision plane remains unsevered, forming a hinge that joins the severed chordal corneal section to the eye. Jet liquid and tissue debris from the cornea are collected and removed by the aspiration groove 77. A second incision may then be made by reiterating these steps to define a wafer of primarily stromal tissue that is removed from the surgical site. Thereafter the hinged flap is returned to impinge on the stromal bed, and may be sutured (or not) or otherwise secured to promote proper healing of the wound. It may be appreciated that proper selection of the applanation member (thickness and curvature) is crucial in properly restructuring the corneal surface to achieve the desired refractive correction. The very high precision construction of the apparatus provides extreme accuracy in the placement and planarity of the incisions, and the narrow, high velocity liquid jet forms an incision with minimal loss of corneal tissue, free of any thermal effects.

With regard to FIGS. 12 and 13, the invention also provides a mechanism for assuring alignment of the jet 97 prior to a surgical incision. A calibration block 101 includes a cylindrical body 102 that includes an end portion 103 adapted to be installed in the stepped opening 26, in a fashion similar to the guide member 61. Quick connect features 87 are provided for easy installation and removal. Extending diametrically through the body 102 is a test bore 104, which is extremely narrow and aligned generally with a meridian of the reticle 74. With the block 101 installed in the instrument and the jet nozzle translated to a zero position (ostensibly aligned with the reticle meridian), the jet may be fired briefly to determine if the jet passes through the test bore and is received by the aspiration groove. The test bore may be approximately $50\mu$ by $100\mu$, or less, and successful fining through the bore 104 demonstrates proper alignment of the zero position of the jet carrier and its servo control system. Alternatively, a laser guide beam described previously may be used to align the system; e.g., the laser beam is directed to intersect and mix with the liquid jet, illuminating the jet and permitting direct visualization that is otherwise difficult or impossible.

Figure 18:
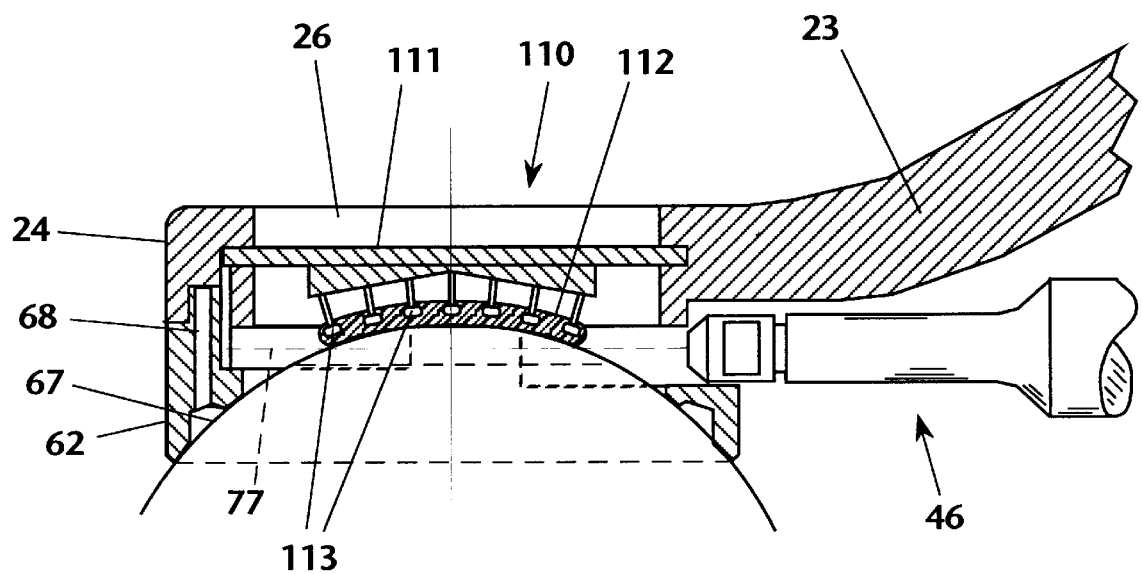
FIG. 18 is a magnified cross-sectional elevation of an alternative embodiment of the invention, showing an adaptive guide member mounted with the jet nozzle of the ophthalmic surgical apparatus of the invention for a surgical procedure on a typical eye.
Figure 19:
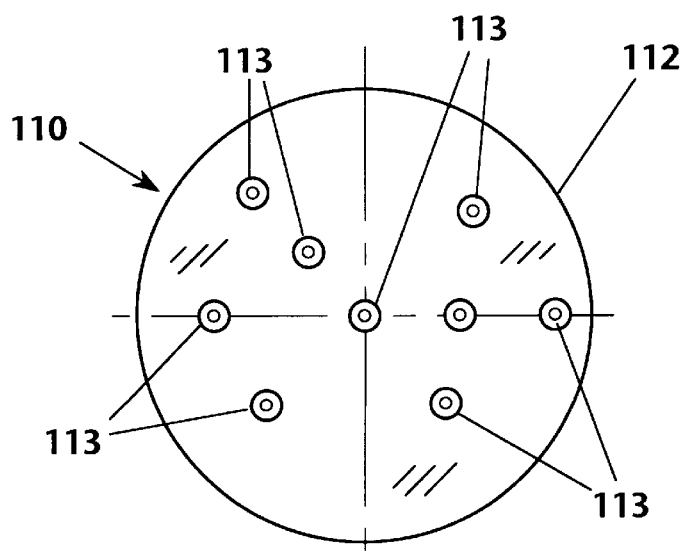
FIG. 19 is a plan view of the adaptive guide member shown in FIG. 18.
Figure 20:
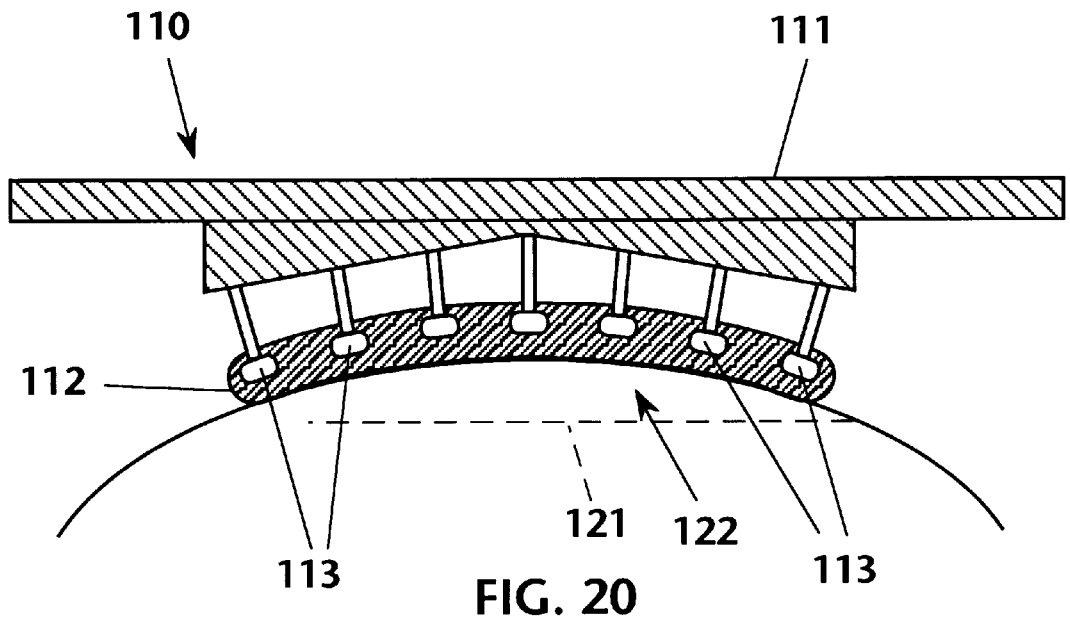
FIG. 20 is a schematic cross-sectional side elevation showing an initial corneal incision formed with the adaptive guide member of FIGS. 18 and 19.

A further embodiment of the invention, shown in FIGS. 18 and 19, incorporates the instrument body and jet carrier structures and assembly substantially as described in the foregoing. The guide member body 62 is also substantially unchanged, except that the applanation member 71 is replaced by an adaptive applanator assembly 110. The assembly 110 incudes a rigid base plate 111 centered on the opening 26, and a flexible curved applanator 112 secured thereto. A plurality of force transducer/force sensor elements 113 are embedded in the applanator 112 and extend to the base plate 111. The elements 113 comprise devices that are capable of precision micro-extension, and are arrayed and utilized in a manner known in the prior art with respect to adaptive optics elements used in imaging systems. The elements 113 may comprise proportional solenoids, piezo ceramic or piezo plastic devices, magnetostrictive devices, shape memory alloy actuators, or the like. The placement of the elements may be a regular array or an asymmetric layout to achieve predetermined applanation characteristics. The conductors leading to the elements 113 may extend through the base plate 111 or may be printed or otherwise deposited on the plate 111, with leads extending to a control system described hereafter.

The curved applanator 112 is provided to impinge on the cornea of the eye undergoing treatment and to selectively alter the curvature of the cornea while resection is carried out by the high velocity liquid jet 77. The adaptive curvature of the applanator 112 eliminates the need for a large plurality of templates (member 71) that are otherwise necessary to cover the range of applanation curvatures required to achieve the desired refractive correction among most patients.

Figure 24:
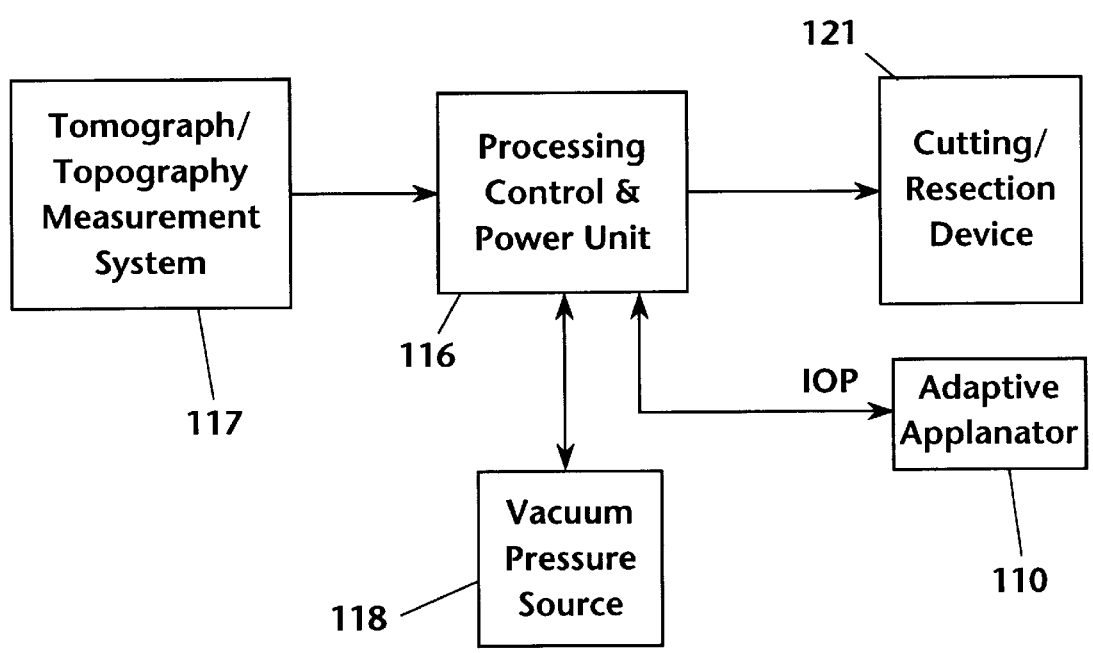
FIG. 24 is a functional block diagram of the control system for the embodiment including the adaptive guide member.

With regard to FIG. 24, the control system for the embodiment of FIGS. 18 and 19 includes a processing control and power unit 116, which includes a microprocessor and associated memory, analog/digital conversion for input and output ports, and programming appropriate for control of the other components of the system. A tomograph/topography measurement system 117 is used to map the corneal surface curvature prior to treatment, and to input this initial curvature into the processing control unit 116, The cutting/resection device 121, which may comprise the liquid jet assembly described previously or an equivalent mechanical or laser device, is also connected to be actuated and controlled by the system 116. Likewise, the vacuum pressure source 118 for the suction ring 67 and aspiration groove 77 is also controlled by the system 116. Most importantly, the control system 116 is connected to the actuators 113 of the adaptive applanator assembly 110, whereby the curvature of the flexible applanator 112 may be selectively altered by the control system 116 to achieve the desired refractive correction.

In addition, the transducers 113 of the adaptive applanator 110 may be employed in a force feedback loop to detect the amount of force applied to the cornea by the member 112. Moreover, the transducers 113 may be used to detect the intra-ocular pressure (IOP) within the cornea, and to measure variations therein. By observing the cyclical variations in IOP that occur in correspondence with the patient's pulse, it is possible and desirable to carry out resection incisions during the brief period between the patient's heart beats, whereby conformal changes due to IOP variations may be neutralized.

FIGS. 20–23 comprise a sequence of views depicting one possible photorefractive surgical technique using the embodiment shown in FIGS. 18, 19, and 24 (instrument body and jet carrier not shown to simplify and clarify). With regard to FIG. 20, the flexible applanator 112 is impinged on the cornea, centered, and the control system 116 is actuated to secure the applanator using the vacuum ring 67. The transducers 113 are actuated to establish an initial curvature for the applanator 112; for example, the applanator 112 conforms to the natural curvature of the cornea. The transducers 113 detect the IOP, and the cutting device 121 is actuated to form a first planar incision 121 during a diastolic pressure phase. The incision 121 extends partially along a chord of the cornea to create an apical flap 122.

Figure 21:
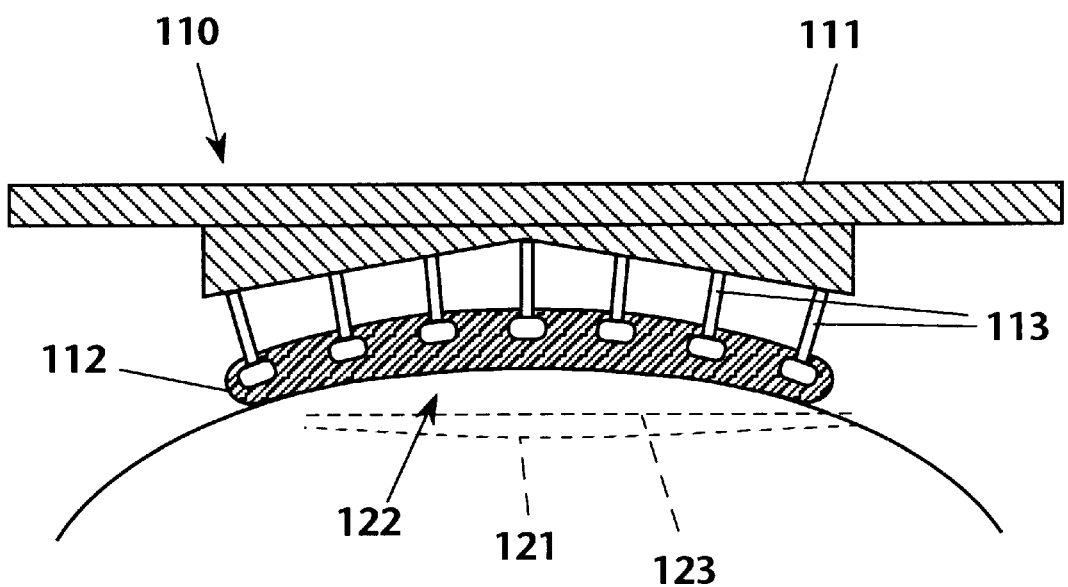
FIG. 21 is a schematic cross-sectional side elevation showing a second corneal incision formed with the adaptive guide member of FIGS. 18–20.
Figure 22:
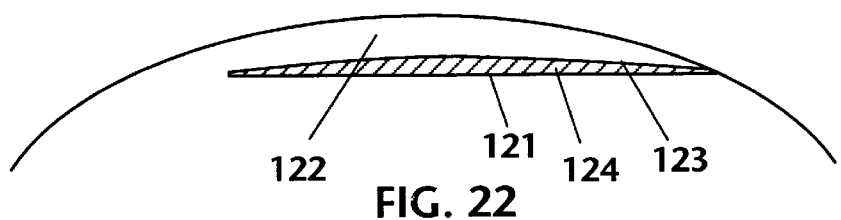
FIG. 22 is a schematic cross-sectional side elevation showing the lenticular corneal wafer formed by the first and second corneal incisions depicted in FIGS. 20 and 21.

Thereafter, with regard to FIG. 21, the transducers 113 of applanator 112 are actuated to impinge on the corneal surface with a predetermined surface conformation differing from the initial curvature. For example, the applanator may be configured to form a curvature having a radius greater that the quiescent corneal radius, thereby flattening the apical portion of the cornea and causing the first planar incision to temporarily assume a concave disposition. A second planar incision 123 is then carried out parallel to the incision 121, preferably also during a diastolic IOP phase. The second incision 123 is disposed in the posterior portion of the apical flap 122. When the conformal pressure of the adaptive applanator is released, as depicted in FIG. 22, the expanding corneal tissue causes the first incision 121 to resume its planar configuration, while the second incision 123 assumes a convex configuration. The result in a convex lenticular tissue wafer 124 formed at the posterior surface of the flap 122. It may be noted that this resection procedure is carried out without any movement or recentration of the instrument body nor replacement or substitution of the guide member.

Figure 23:
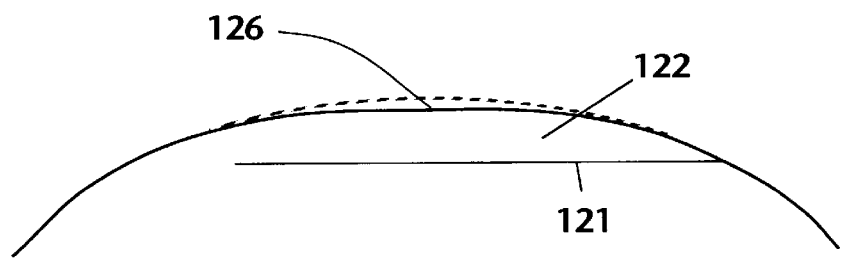
FIG. 23 is a schematic side elevation showing the altered cornea conformation resulting from removal of the lenticular cornea wafer of FIG. 22.

The lenticular tissue wafer 124 is then removed, using forceps or other surgical instruments, so that the apical flap 122 may slump onto the stromal bed formed by the planar incision 121. Healing of the resection is facilitated by stabilizing the flap 122, whether by suture, gravity, adhesive, or the like. As shown in FIG. 23, the apex of the cornea thus assumes a revised curvature 126; in the case depicted, a flattened convex conformation that alters the refractive characteristic of the eye. It is apparent that the shape of the lenticular tissue wafer 123 determines the ultimate refractive correction thus obtained, and the shape of the lenticular tissue wafer 122 is determined by the variable applanation effect applied selectively by the member 112.

In the description of the instruments and methods herein, the reference to a liquid jet is intended to encompass a jet of any liquid or flowable material having sufficient velocity and kinetic energy to carry out the tissue cutting as described. The liquid may comprise sterile water or sterile saline solution. The invention includes the use of a balanced electrolyte solution, which is least inflammatory to the cut surfaces of the incisions. For harder or denser tissue types, the liquid may comprise a suspension of fine abrasive particles in any suitable carrier liquid, and this abrasive slurry may hasten the cutting process.

The foregoing description of the preferred embodiment of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and it practical application to thereby enable others skilled in the art to best utilize the invention in various embodiments and with various modifications as suited to the particular purpose contemplated. It is intended that the scope of the invention be defined by the claims appended hereto.

We claim:

1. An apparatus for ophthalmic surgery, including:

a jet nozzle for emitting a fine diameter, high velocity liquid jet in a longitudinal direction, said jet being capable of cutting corneal tissue;

jet carrier means for supporting said jet nozzle;

an instrument body;

means for releasably securing said instrument body to the corneal portion of an eye;

means for securing said jet carrier means to said instrument body in translatable fashion along a translation axis intersecting said longitudinal direction;

means for translating said jet carrier selectively with precise positional control along said translation axis to sweep said liquid jet through a portion of the corneal tissue of an eye secured to said instrument body and effect an incision in said corneal tissue;

at least one guide member for controlling placement and conformation of the incision in the corneal tissue formed by said high velocity liquid jet;

said guide member further including quick connect means for releasably securing said guide member to said instrument body.

2. The apparatus for ophthalmic surgery of claim 1, wherein said guide member includes suction ring means formed integrally therein and disposed to releasably secure the corneal portion of the eye undergoing surgery.

3. The apparatus for ophthalmic surgery of claim 2, wherein said guide member further includes an applanation plate formed integrally therein and disposed to deform a segment of the corneal portion undergoing surgery.

4. The apparatus for ophthalmic surgery of claim 3, wherein said applanation plate includes an applanation surface disposed to impinge on said segment of the corneal portion, said applanation surface having a predetermined curvature to be imparted to said segment of the corneal portion during the surgical procedure.

5. The apparatus for ophthalmic surgery of claim 4, wherein said applanation plate is formed of transparent material for direct visualization of the corneal portion during the surgical procedure.

6. The apparatus for ophthalmic surgery of claim 5, wherein said applanation plate further includes an outer surface obverse to said applanation surface, and reticle means on said outer surface for aligning said guide member and guiding and measuring the surgical incision in the corneal portion.

7. The apparatus for ophthalmic surgery of claim 4, further including a plurality of guide members interchangeably secured by said quick connect means to said instrument body, said plurality of guide members having differing applanation plate thicknesses and differing applanation surface curvatures.

8. The apparatus for ophthalmic surgery of claim 4, wherein said instrument body includes a distal end having an opening extending therethrough, said quick connect means releasably securing any one of said plurality of guide members in said opening.

9. The apparatus for ophthalmic surgery of claim 8, further including calibration means for aligning said high velocity liquid jet at a defined position with respect to said instrument body prior to a surgical procedure.

10. The apparatus for ophthalmic surgery of claim 9, wherein said calibration means includes a calibration block dimensioned to be received in said opening of said distal end of said instrument body and secured therein by said quick connect means.

11. The apparatus for ophthalmic surgery of claim 10, wherein said calibration block includes a narrow linear passage extending therethrough and aligned coaxially with said defined position, whereby said liquid jet passes through said narrow linear passage only if said jet carrier is disposed at said defined position.

12. The apparatus for ophthalmic surgery of claim 3, wherein said guide member includes a closed curved sidewall, said applanation plate secured within an upper portion of said closed curved sidewall.

13. The apparatus for ophthalmic surgery of claim 12, wherein a lower portion of said closed curved sidewall defines a lower opening adapted to impinge on the eye undergoing surgery, said suction ring means disposed concentrically at said lower opening.

14. The apparatus for ophthalmic surgery of claim 13, further including jet slot means formed in said closed curved sidewall for receiving and guiding said jet nozzle.

15. The apparatus for ophthalmic surgery of claim 14, wherein said jet slot means includes a jet slot extending chordally in said closed curved sidewall, said jet slot having a width sufficient to receive said jet nozzle with minimal clearance for translation therein along said translation axis.

16. The apparatus for ophthalmic surgery of claim 15, further including aspiration means for removing liquid from said liquid jet and tissue debris from the surgical incision from said lower opening of said applanation member.

17. The apparatus for ophthalmic surgery of claim 16, wherein said aspiration means includes an aspiration groove formed in an interior surface of said closed curved sidewall, said aspiration groove extending in diametrical opposition to said jet slot.

18. The apparatus for ophthalmic surgery of claim 17, wherein said instrument body includes a distal end having an opening extending therethrough, said quick connect means releasably securing said guide member in said opening.

19. The apparatus for ophthalmic surgery of claim 18, further including suction passage means in said distal end for communicating with said suction ring of said guide member.

20. The apparatus for ophthalmic surgery of claim 18, further including aspiration passage means in said distal end for communicating with said aspiration groove in said guide member.

21. An apparatus for ophthalmic surgery, including:
a jet nozzle for emitting a fine diameter, high velocity liquid jet in a longitudinal direction, said jet being capable of cutting corneal tissue;
jet carrier means for supporting said jet nozzle;
an instrument body;
means for releasably securing said instrument body to the corneal portion of an eye;
means for securing said jet carrier means to said instrument body in translatable fashion along a translation axis intersecting said longitudinal direction;
means for translating said jet carrier selectively with precise positional control along said translation axis to sweep said liquid jet through a portion of the corneal tissue of an eye secured to said instrument body and effect an incision in said corneal tissue;
said means for translating said jet carrier including a micro-motor assembly secured in said instrument body, and a pinion gear connected to the output of said micro-motor assembly and protruding from said instrument body.

22. The apparatus for ophthalmic surgery of claim 21, further including a rack gear secured to said jet carrier and disposed to engage said pinion gear in translationally driven relationship.

23. The apparatus for ophthalmic surgery of claim 22, wherein said means for translating includes a pair of micro-precision crossed roller slides secured to said jet carrier parallel to said translation axis and supporting said instrument body in freely translating fashion.

24. An apparatus for ophthalmic surgery, including:
a jet nozzle for emitting a fine diameter, high velocity liquid jet in a longitudinal direction, said jet being capable of cutting corneal tissue;
jet carrier means for supporting said jet nozzle;
an instrument body;
means for releasably securing said instrument body to the corneal portion of an eye;
means for securing said jet carrier means to said instrument body in translatable fashion along a translation axis intersecting said longitudinal direction;
means for translating said jet carrier selectively with precise positional control along said translation axis to sweep said liquid jet through a portion of the corneal tissue of an eye secured to said instrument body and effect an incision in said corneal tissue; and,
a guide member for controlling placement and conformation of incisions in the corneal tissue formed by said high velocity liquid jet;
said guide member including adaptive applanator means defining a selectively variable curved surface for impinging on the apex of the cornea.

25. An apparatus for ophthalmic surgery, including:
cutting means capable of cutting corneal tissue;
an instrument body, and means for releasably securing said instrument body to the corneal portion of an eye;
translating means supported on said instrument body for moving said cutting means through a portion of the cornea secured to said instrument body to form an incision in the cornea;

adaptive applanator means for impinging on the corneal portion of the eye, said adaptive applanator means including a selectively variable curved surface impinging on the corneal portion to temporarily alter the curvature of the outer surface of the corneal portion in a predetermined manner.

26. The apparatus for ophthalmic surgery of claim 25, wherein said adaptive applanator means includes a generally rigid base and a flexible curved applanator member, and transducer means extending between said base and said applanator member to selectively alter the curvature of said applanator member with respect to said base.

27. The apparatus for ophthalmic surgery of claim 26, wherein said transducer means includes a plurality of transducers extending between said base and said applanator member.

28. The apparatus for ophthalmic surgery of claim 26, wherein said transduce r means further includes means for sensing variations in intraocular pressure within the corneal portion.

29. The apparatus for ophthalmic surgery of claim 28, further including means for actuating said translating means during a selected phase of said variations in intraocular pressure within the corneal portion.

30. An apparatus for ophthalmic surgery, including:
    a jet nozzle for emitting a fine diameter, high velocity liquid jet in a longitudinal direction, said jet being capable of cutting corneal tissue;
    jet carrier means for supporting said jet nozzle;
    an instrument body;
    means for releasably securing said instrument body to the corneal portion of an eye;
    means for securing said jet carrier means to said instrument body in translatable fashion along a translation axis intersecting said longitudinal direction;
    means for translating said jet carrier selectively along said translation axis to sweep said liquid jet through a portion of the corneal tissue of an eye secured to said instrument body and effect an incision in said corneal tissue; and,
    safety shutter means for selectively blocking said high velocity liquid jet.

31. The apparatus for ophthalmic surgery of claim 30, wherein said safety shutter means includes a sheathed cable assembly having a movable distal end disposed to translate between a first position in which said liquid jet is blocked, and a second position in which said liquid jet is unimpeded.

32. The apparatus for ophthalmic surgery of claim 31, further including means for biasing said distal end toward said first position.

33. An apparatus for ophthalmic surgery, including:
    a jet nozzle for emitting a fine diameter, high velocity liquid jet in a longitudinal direction, said jet being capable of cutting corneal tissue;
    jet carrier means for supporting said jet nozzle;
    an instrument body;
    means for releasably securing said instrument body to the corneal portion of an eye;
    means for securing said jet carrier means to said instrument body in translatable fashion along a translation axis intersecting said longitudinal direction;
    means for translating said jet carrier selectively along said translation axis to sweep said liquid jet through a portion of the corneal tissue of an eye secured to said instrument body and effect an incision in said corneal tissue; and,
    aiming beam means for permitting direct visualization of said high velocity liquid jet.

34. The apparatus for ophthalmic surgery of claim 33, wherein said aiming beam means includes a narrow beam light source directed to intersect and mix with said liquid jet.

35. The apparatus for ophthalmic surgery of claim 34, wherein said narrow beam light source includes a light emitting diode.

36. The apparatus for ophthalmic surgery of claim 34, wherein said narrow beam light source includes a laser diode.

37. A method for resection of the cornea, including the steps of:
    providing an adaptive applanator having a applanation surface of selectively variable conformation;
    securing said adaptive applanator to the corneal portion of an eye while said applanation surface is disposed in a first selected curvature and impinged on the corneal portion;
    forming a first lateral surgical incision in the corneal portion to create an apical flap;
    reconfiguring said adaptive applanator to cause said applanation surface to adopt a second selected curvature impinging on said corneal portion;
    forming a second lateral surgical incision in the corneal portion, said first and second lateral surgical incsions defining a lenticular wafer of corneal tissue;
    removing said lenticular wafer; and,
    replacing said apical flap on the stromal bed of the removed lenticular wafer.

38. The method of claim 37, wherein said steps of forming the first incision, reconfiguring the adaptive applanator, and forming the second incision are carried out without removing said adaptive applanator from the corneal portion.

39. The method of claim 37, wherein said second lateral incision is formed in a posterior portion of said apical flap.

40. The method of claim 37, wherein said first and second incisions are generally planar and parallel.

41. The method of claim 39, further including the steps of forming said first and second incisions by a high velocity, fine diameter liquid jet.

42. A method for resection of the cornea, including the steps of:
    providing a plurality of guide members, said guide members having applanator plates of various thicknesses and applanation surface curvatures;
    providing a surgical instrument having linear cutting means tranversing a planar path; said planar path being closely spaced apart from the applanation surface of a guide member;
    securing one of said guide members in the surgical instrument, said one guide member having a predetermined spacing of said applanation surface from said planar path;
    operating said linear cutting means to form a first lateral incision in the cornea and create an apical flap;
    removing said one guide member from said instrument body and securing a second guide member in said instrument body, said second guide member having a second predetermined spacing of said applanation surface from said planar path;
    operating said linear cutting means to form a second lateral incision in the cornea and create an lenticular wafer of corneal tissue;
    removing said lenticular wafer; and,
    replacing said apical flap on the stromal bed of the removed lenticular wafer.

* * * * *